United States Patent

Krüger et al.

Patent Number: 6,054,459
Date of Patent: Apr. 25, 2000

[54] SUBSTITUTED 1,2,3,4-TETRAHYDRO-5-NITRO-PYRIMIDINES

[75] Inventors: Bernd-Wieland Krüger, Bergisch Gladbach; Hermann Uhr, Krefeld; Johannes Kanellakopulos, Hilden; Ernst-Rudolf Gesing, Erkrath-Hochdahl; Hilmar Wolf, Langenfeld; Andreas Turberg, Erkrath; Norbert Mencke, Leverkusen; Christoph Erdelen, Leichlingen; Ulrike Wachendorff-Neumann, Neuwied; Jürgen Hartwig, Leichlingen, all of Germany

[73] Assignee: Bayer Aktiengesellschaft, Leverkusen, Germany

[21] Appl. No.: 09/177,940

[22] Filed: Oct. 23, 1998

Related U.S. Application Data

[62] Division of application No. 08/676,272, filed as application No. PCT/EP95/00058, Jan. 9, 1995, Pat. No. 5,869,491.

[30] Foreign Application Priority Data

Jan. 21, 1994 [DE] Germany ............... 44 01 635

[51] Int. Cl.[7] ............... C07D 239/06; A61K 31/505
[52] U.S. Cl. ............... 514/256; 544/328; 544/327
[58] Field of Search ............... 514/256; 544/322, 544/328, 327

[56] References Cited

U.S. PATENT DOCUMENTS 4,900,825 2/1990 Koehler ............... 544/328

FOREIGN PATENT DOCUMENTS

| 247 477 | 2/1987 | European Pat. Off. . |
|---|---|---|
| 316 843 | 5/1989 | European Pat. Off. . |
| 366 085 | 5/1990 | European Pat. Off. . |
| 375 613 | 6/1990 | European Pat. Off. . |
| 0 407 594 | 11/1990 | European Pat. Off. . |
| 398 084 | 11/1990 | European Pat. Off. . |
| 3-264580 | 11/1991 | Japan . |
| WO 90/05134 | 3/1990 | WIPO . |
| WO 94/05670 | 3/1994 | WIPO . |

OTHER PUBLICATIONS

Patent Abstracts of Japan, vol.16, No.71 (1991) (English Abstract of WO 90/05134.

*Primary Examiner*—John M. Ford
*Attorney, Agent, or Firm*—Joseph C. Gil; Carol Marmo

[57] ABSTRACT

The present invention relates to new substitued 1,2,3,4-tetrahydro-5-nitro-pyrimidines of the formula (I)

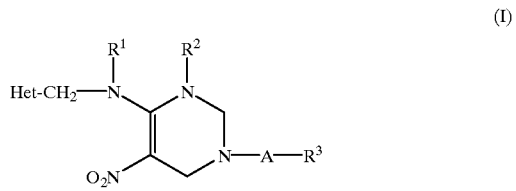

(I)

in which
Het represents optionally substituted pyridyl or thiazolyl,
$R^1$ represents $C_{1-4}$-alkyl,
$R^2$ represents $C_{1-4}$-alkyl,
$R^1$ and $R^2$ together with the adjacent atoms form a saturated 5- or 6-membered ring which optionally contains N or O as further hetero atom and which is optionally substituted,
A represents straight-chain or branched alkylene having at least 2 C atoms which is optionally substituted by phenyl, halogen, OH, CN or the radical $NR^4R^5$, where $R^4$ and $R^5$ represent hydrogen, $C_{1-4}$-alkyl or phenyl, and which is optionally interrupted,
$R^3$ represents one of the radicals

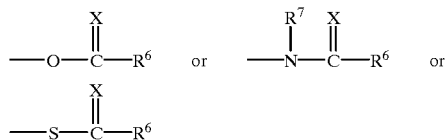

wherein the variables are herein below defined.

5 Claims, No Drawings

SUBSTITUTED 1,2,3,4-TETRAHYDRO-5-NITRO-PYRIMIDINES

This application is a divisional of application Ser. No. 08/676,272, filed on Jul. 12, 1996 now U.S. Pat. No. 5,869,491 which is a national stage of PCT/EP95/00058 filed Jan. 9, 1995.

The present invention relates to new substituted 1,2,3,4-tetrahydro-5-nitro-pyrimidines, to processes for their preparation, and to their use in pesticides, in particular as insecticides.

In addition, the new compounds have a highly pronounced ectoparasiticidal activity.

Furthermore, it is known that certain nitrated nitrogen heterocycles have insecticidal properties (cf. EP 0 316 843; EP 0 375 613).

The new substituted 1,2,3,4-tetrahydro-5-nitro-pyrimidines of the formula (I) have been found,

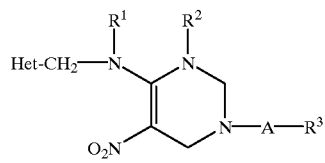

(I)

in which
Het represents optionally substituted pyridyl or thiazolyl,
$R^1$ represents $C_{1-4}$-alkyl,
$R^2$ represents $C_{1-4}$-alkyl,
$R^1$ and $R^2$ together with the adjacent atoms form a saturated 5- or 6-membered ring which optionally contains N or O as further hetero atom and which is optionally substituted,
A represents straight-chain or branched alkylene having at least 2 C atoms which is optionally substituted by phenyl, halogen, OH, CN or the radical $NR^4R^5{}_1$ where $R^4$ and $R^5$ represent hydrogen, $C_{1-4}$-alkyl or phenyl, and which is optionally interrupted once or more than once by O, S,

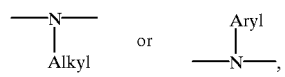

A furthermore represents optionally substituted cycloalkylene,
$R^3$ represents one of the radicals

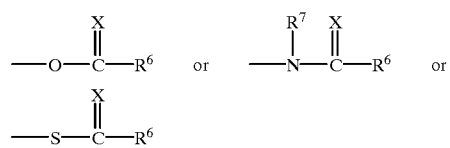

where
$R^6$ represents alkyl, cycloalkyl, alkenyl, aryl, aralkyl, heteroaryl, alkoxy, cycloalkoxy, alkenoxy, aryloxy, aralkoxy, heteroaryloxy, alkylthio, arylthio, aralkylthio, heteroarylthio, amino, alkylamino, dialkylamino, arylamino, aryl-alkylamino, aralkylamino, aralkyl-alkylamino, it being possible for the radicals to be optionally substituted,
X represents oxygen or sulphur, and
$R^7$ represents hydrogen or $C_{1-4}$-alkyl.

Furthermore, it has been found that the substituted 1,2,3,4-tetrahydro-5-nitro-pyrimidines of the formula (I) are obtained when a) nitromethylene derivatives of the formula (II)

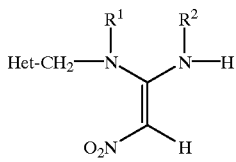

(II)

in which
Het, $R^1$ and $R^2$ have the abovementioned meanings, are reacted with amines of the formula (III), $$H_2N\text{-}A\text{-}R^3 \qquad (III)$$

in which
A and $R^3$ have the abovementioned meanings,
in the presence of at least twice the molar amount of formaldehyde, if appropriate in the presence of acidic catalysts and if appropriate in the presence of diluents,
or b) in the event that, in formula (I), $R^3$ represents the radical

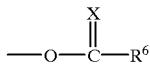

or the radical

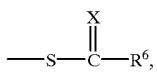

nitromethylene derivatives of the formulae IV or IVa

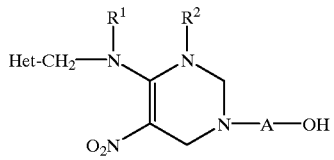

(IV)

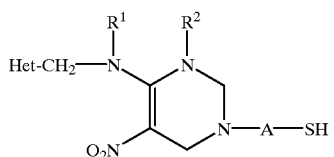

(IVa)

in which
Het, $R^1$, $R^2$ and A have the abovementioned meanings, are reacted with compounds of the formula (V)

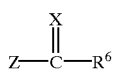 (V)

in which

Z represents a leaving group, such as halogen, or the radical

, and

X and $R^6$ have the abovementioned meanings, or with compounds of the formula (VI)

XCN-$R^9$ (VI)

in which

X represents O or S and $R^9$ represents one of the following radicals alkyl, aryl or aralkyl which have been mentioned under $R^6$, if appropriate in the presence of an acid-binding agent and if appropriate in the presence of diluents and/or catalysts, or c) in the event that, in formula (I), $R^1$ and $R^2$ together with the adjacent atoms do not cyclize, nitro-methylene derivatives of the formula (A)

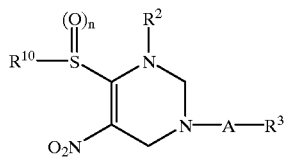 (A)

in which $R^{10}$ represents $C_1$–$C_4$-alkyl or phenyl, n assumes values of 0, 1 or 2 and $R^2$, $R^3$ and A have the abovementioned meanings are reacted with amines of the formula (B)

Het—$CH_2NHR^1$ (B)

in which

Het and $R^1$ have the abovementioned meanings, if appropriate in the presence of an acid-binding agent and if appropriate of diluents and/or catalysts.

The present invention also relates to the nitromethylene derivatives of the formulae (IVb), (IVc) and (IVd)

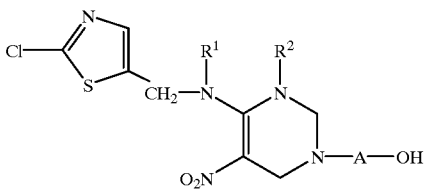 (IVb)

in which $R_1$, $R^2$ and A have the abovementioned meanings,

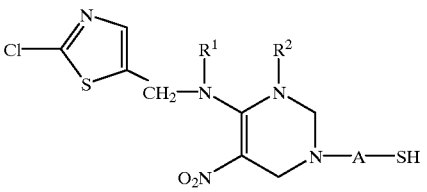 (IVc)

in which, $R^1$, $R^2$ and A have the abovementioned meanings,

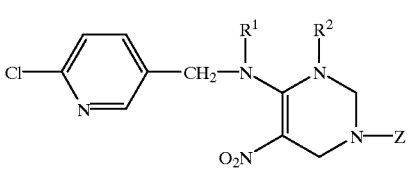 (IVd)

in which $R^1$ and $R^2$ have the abovementioned meanings and Z represents

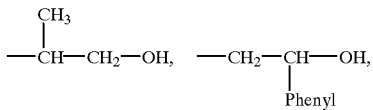

Optionally substituted alkyl in the general formulae denotes straight-chain or branched alkyl having preferably 1 to 12, in particular 1 to 6, carbon atoms. The following may be mentioned by way of example and as being preferred: optionally substituted methyl, ethyl, n- and i-propyl and n-, i- and t-butyl.

Optionally substituted alkenyl and the alkenyl moiety of optionally substituted alkenyloxy and alkenylthio in the general formulae denote straight-chain or branched alkenyl having preferably 2 to 6, in particular 2 to 4, carbon atoms. The following may be mentioned by way of example and as being preferred: optionally substituted ethenyl, propene-1-yl, propene-2-yl and butene-3-yl.

Optionally substituted cycloalkyl or cycloalkylene in the general formulae denotes mono-, bi- and tricyclic cycloalkyl having preferably 3 to 10, in particular 3, 5 or 6, carbon atoms. The following may be mentioned by way of example and as being preferred: optionally substituted cyclopropyl, cyclobutyl, cyclopentyl, cyclohexyl, cycloheptyl, bicyclo[2, 2,2]octyl and adamantyl.

Optionally substituted alkoxy in the general formulae denotes straight-chain or branched alkoxy having preferably 1 to 6, in particular 1 to 4, carbon atoms. The following may be mentioned by way of example and as being preferred: optionally substituted methoxy, ethoxy, n- and i-propoxy and n-, s- and t-butoxy.

Optionally substituted alkylthio in the general formulae denotes straight-chain or branched alkylthio having preferably 1 to 6, in particular 1 to 4, carbon atoms. The following may be mentioned by way of example and as being preferred: optionally substituted methylthio, ethylthio, n- and i-propylthio and n-, s- and t-butylthio.

Optionally substituted aryl, such as the aryl moiety of aryloxy, arylthio and arylamino in the general formulae, preferably denotes optionally substituted phenyl or naphthyl, in particular phenyl.

Optionally substituted aralkyl and the arylkyl moiety of aralkoxy, aralkylthio and aralkylamino in the general formulae denotes aralkyl which is optionally substituted in the aryl moiety and/or alkyl moiety and which has preferably 6 or 10, in particular 6, carbon atoms in the aryl moiety (preferably phenyl or naphthyl, in particular phenyl) and preferably 1 to 4, in particular 1 or 2, carbon atoms in the alkyl moiety, it being possible for the alkyl moiety to be straight-chain or branched. The following may be mentioned by way of example and as being preferred: optionally substituted benzyl and phenylethyl.

Heteroaryl in the general formulae preferably denotes heteroaromatic 5- to 7-membered rings having preferably 1 to 3, in particular 1 or 2, identical or different hetero atoms or hetero groups. The hetero atoms are oxygen, sulphur or nitrogen. Radicals which may preferably be mentioned are furyl, thiophenyl, pyrazolyl, imidazolyl, 1,2,3- and 1,2,4-triazolyl, oxazolyl, isoxazolyl, thia zolyl, isothiazolyl, 1,2, 3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl.

The optionally substituted radicals in the general formulae can have attached one or more, preferably 1 to 3, in particular 1 or 2, identical or different substituents. The following may preferably be mentioned as substituents:

Alkyl having preferably 1 to 4, in particular 1 or 2, carbon atoms, such as methyl, ethyl, n- and i-propyl and n-, i- and t-butyl; cycloalkyl, cycloalkylamino or cycloalkylalkyl having preferably 3 to 7, in particular 5 or 6, carbon atoms in the cycloalkyl moiety and preferably 1 to 5, in particular 1 to 4, carbon atoms in the straight-chain or branched alkyl moiety; aralkyl, preferably phenylalkyl having preferably 1 to 4, in particular 1 to 3, carbon atoms in the alkyl moiety; alkoxy having preferably 1 to 4, in particular 1 or 2, carbon atoms, such as methoxy, ethoxy, n- and i-propoxy and n-, i- and t-butoxy, alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different and preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino or mono- and dialkylaminocarbonyl having preferably 1 to 4, in particular 1 or 2, carbon atoms per alkyl group, such as methylamino, methyl-ethyl-amino, n- and i-propyl-amino and methyl-n-butylamino; carboxyl; carbalkoxy having preferably 2 to 4, in particular 2 or 3, carbon atoms, such as carbomethoxy and carboethoxy; sulpho (—SO$_3$H) alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl.

The pyridyl and thiazolyl radicals in the definition of Het have attached preferably 1 or 2 identical or different substituents, substitutuents which may be mentioned preferably being halogen (fluorine, chlorine, bromine and iodine, preferably fluorine or chlorine, in particular chlorine) or methyl. Het particularly preferably represents 2-chloro-1, 3-thiazol-5-yl and 2-chloropyridin-5-yl.

The definitions which have been mentioned here as being preferred also apply analogously to the preferred combinations of definitions which are mentioned hereinbelow.

Surprisingly, the substituted 1,2,3,4-tetrahydro-5-nitropyrimidines of the formula (I) according to the invention are distinguished in an outstanding manner by a powerful activity as insecticides and ectoparasiticides.

The invention preferably relates to compounds of the formula (I) in which

Het represents pyridyl which is optionally substituted by halogen or thiazolyl which is optionally substituted by halogen, $R^1$ represents methyl or ethyl, $R^2$ represents methyl or ethyl, $R^1$ and $R^2$ together with the adjacent atoms form a saturated 5- or 6-membered ring which is optionally substituted by OH or $C_{1-4}$-alkyl, such as, for example,

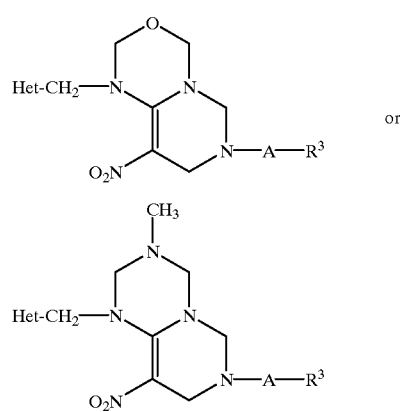

where

Het, A and $R^3$ have the abovementioned meanings,

A represents straight-chain or branched alkylene having 2 to 6 C atoms which can optionally be substituted by phenyl, halogen, OH, CN, amino or mono- or di-$C_{1-4}$alkylamino, and A furthermore represents cyclopropylene, methylcyclopropylene, cyclohexylene or cyclooctylene, $R^3$ represents one of the radicals

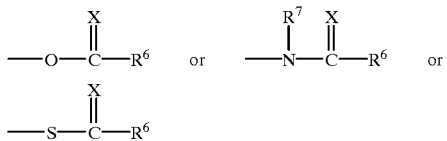

where $R^6$ represents $C_{1-8}$-alkyl, $C_{3-8}$-cycloalkyl, $C_{2-8}$-alkenyl, phenyl, benzyl, pyridyl, imidazolyl, pyrazolyl, thiazolyl, oxazolyl, pyrrolyl, phenylethyl, $C_{1-8}$-alkoxy, $C_{3-8}$-cycloalkoxy, $C_{3-8}$-alkenoxy, phenoxy, benzyloxy, phenylethyloxy, $C_{1-8}$-alkylthio, phenylthio, benzylthio, phenylethylthio, amino, $C_{1-4}$-alkylamino, di-$C_{1-4}$-alkylamino, phenylamino, N-phenyl-N-$C_{1-4}$-alkylamino or phenyl-$C_{1-4}$-alkyl-amino, N-phenyl-$C_{1-4}$-alkyl-N-$C_{1-4}$-alkyl-amino, it being possible for these radicals to be optionally substituted by one or more identical or different substituents from amongst the preferred or particularly preferred substituents mentioned above, $R^7$ represents hydrogen or $C_1$–$C_4$-alkyl and X represents oxygen or sulphur.

Particularly preferred compounds of the formula (I) are those in which

Het represents

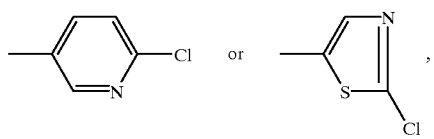

$R^1$ represents methyl or ethyl, $R^2$ represents methyl or ethyl, $R^1$ and $R^2$ together with the adjacent atoms represent a saturated 5- or 6-membered ring, in particular the ring below,

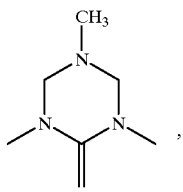

A represents ethylene, propylene or butylene, each of which can optionally be substituted by halogen, in particular fluorine or chlorine, or by phenyl, and A furthermore represents cyclohexylene, $R^3$ represents one of the radicals

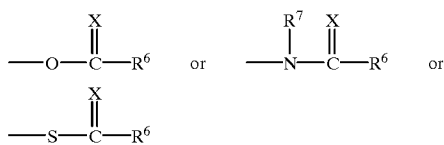

where $R^6$ represents $C_{1-6}$-alkyl, such as methyl, ethyl, n-propyl, i-propyl, s-butyl, t-butyl, n-hexyl, methoxy, ethoxy, n- or i-propoxy, methylamino, dimethylamino, ethylamino, diethylamino, ethylmethylamino, n-propylamino, di-(n-propyl)amino, methyl(n-propyl)amino, ethyl(n-propyl)amino, methylisopropylamino, ethylisopropylamino, isopropyl(n-propyl)amino, cyclopentyl, cyclohexyl, cyclopentylmethyl, cyclopentylethyl, cyclopentyl-n-propyl, cyclopentylisopropyl, cyclohexylmethyl, cyclohexylethyl, cyclohexyl-n-propyl, cyclohexylisopropyl, phenylmethyl, phenylethyl, phenyl-n-propyl and/or phenyl-isopropyl, phenyl, pyridyl, imidazolyl, thiazolyl, oxazolyl, phenoxy, $C_{1-4}$-alkylthio such as methylthio, ethylthio, n- or i-propylthio, phenylthio, it being possible for the radicals to be optionally substituted by $C_{1-4}$-alkyl, halogen such as fluorine or chlorine, or CN, $R^7$ represents methyl or hydrogen and X represents sulphur or oxygen.

Examples of the compounds of the formula (I) according to the invention are listed in Tables 1 to 128 below.

TABLE 1

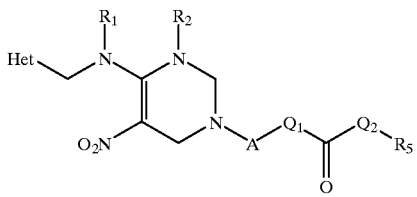

(I-1)

Compounds of Table 1 are those of the general formula (II), in which Het=2-chloropyridin-5-yl, $R_1$=Me, $R_2$=Me, A=$CH_2CH_2$—, $Q_1$=O, $Q_2$=O, and $R_5$ is as defined below:

Me represents methyl, Et represents ethyl, Pr represents propyl, Bu represents butyl

| Compound No. | $R_5$ |
|---|---|
| 1 | Me |
| 2 | Et |
| 3 | Pr |
| 4 | i-Pr |
| 5 | cyclo-Pr |
| 6 | n-Bu |
| 7 | t-Bu |
| 8 | —$CH_2$-t-Bu |
| 9 | —$CH_2(CH_2)_5Cl$ |

Table 2

Table 2 contains the compounds of the general formula (I-1), in which Het=2-chloropyridin-5-yl, $R_1$=Me, $R_2$=Me, A=—$CH_2CH_2$—, $Q_1$=O, $Q_2$=NH and $R_5$ is defined as listed in Table 1.

Table 3

Table 3 contains the compounds of the general formula (I-1), in which Het=2-chloropyridin-5-yl, $R_1$=Me, $R_2$=Me, A=—$CH_2CH_2$—, $Q_1$=NH, $Q_2$=O and $R_5$ is defined as listed in Table 1.

Table 4

Table 4 contains the compounds of the general formula (I-1), in which Het=2-chloropyridin-5-yl, $R_1$=Me, $R_2$=Me, A=—$CH_2CH_2$—, $Q_1$=NH, $Q_2$=NH and $R_5$ is defined as listed in Table 1.

Table 5

Table 5 contains the compounds of the general formula (I-1), in which Het=2-chloropyridin-5-yl, $R_1$=Me, $R_2$=Me, A=—$CH_2CH_2CH_2$—, $Q_1$=O, $Q_2$=O and $R_5$ is defined as listed in Table 1.

Table 6

Table 6 contains the compounds of the general formula (I-1), in which Het=2-chloropyridin-5-yl, $R_1$=Me, $R_2$=Me, A=—$CH_2CH_2CH_2$—, $Q_1$=O, $Q_2$=NH and $R_5$ is defined as listed in Table 1.

Table 7

Table 7 contains the compounds of the general formula (I-1), in which Het=2-chloropyridin-5-yl, $R_1$=Me, $R_2$=Me, A=—$CH_2CH_2CH_2$—, $Q_2$=NH, $Q_2$=O and $R_5$ is defined as listed in Table 1.

Table 8

Table 8 contains the compounds of the general formula (I-1), in which Het=2-chloropyridin-5-yl, $R_1$=Me, $R_2$=Me, A=—$CH_2CH_2CH_2$—, $Q_1$=NH, $Q_2$=NH and $R_5$ is defined as listed in Table 1.

Table 9

Table 9 contains the compounds of the general formula (I-1), in which Het=2-chloropyridin-5-yl, $R_1$=Me, $R_2$=Me, A=—$CH(CH_3)CH_2$—, $Q_1$=O, $Q_2$=O and $R_5$ is defined as listed in Table 1.

Table 10

Table 10 contains the compounds of the general formula (I-1), in which Het=2-chloropyridin-5-yl, $R_1$=Me, $R_2$=Me, A=—$CH(CH_3)CH_2$—, $Q_1$=O, $Q_2$=NH and $R_5$ is defined as listed in Table 1.

Table 11

Table 11 contains the compounds of the general formula (I-1), in which Het=2-chloropyridin-5-yl, $R_1$=Me, $R_2$=Me, A=—$CH(CH_3)CH_2$—, $Q_1$=NH, $Q_2$=O and $R_5$ is defined as listed in Table 1.

Table 12

Table 12 contains the compounds of the general formula (I-1), in which Het=2-chloropyridin-5-yl, $R_1$=Me, $R_2$=Me, A=—$CH(CH_3)CH_2$—, $Q_1$=NH, $Q_2$=NH and $R_5$ is defined as listed in Table 1.

Table 13

Table 13 contains the compounds of the general formula (I-1), in which Het=2-chloropyridin-5-yl, $R_1$=Me, $R_2$=Me, A=—$CH_2CH(CH_3)$—, $Q_1$=O, $Q_2$=O and $R_5$ is defined as listed in Table 1.

Table 14

Table 14 contains the compounds of the general formula (I-1), in which Het=2-chloropyridin-5-yl, $R_1$=Me, $R_2$=Me, A=—$CH_2CH(CH_3)$—, $Q_1$=O, $Q_2$=NH and $R_5$ is defined as listed in Table 1.

Table 15

Table 15 contains the compounds of the general formula (I-1), in which Het=2-chloropyridin-5-yl, $R_1$=Me, $R_2$=Me, A=—$CH_2CH(CH_3)$—, $Q_1$=NH, $Q_2$=O and $R_5$ is defined as listed in Table 1.

Table 16

Table 16 contains the compounds of the general formula (I-1), in which Het=2-chloropyridin-5-yl, $R_1$=Me, $R_2$=Me, A=—$CH_2CH(CH_3)$—, $Q_1$=NH, $Q_2$=NH and $R_5$ is defined as listed in Table 1.

Tables 17 to 32

Each one of Tables 17 to 32 contains the compounds of the general formula (I-1), in which
A, $Q_1$, $Q_2$ and $R_5$ have the meanings as shown in Tables 1 to 16,
Het=2-chloropyridin-5-yl, $R_1$=Me and $R_2$=Et.

Tables 33 to 48

Each one of Tables 33 to 48 contains the compounds of the general formula (I-1), in which
A, $Q_1$, $Q_2$ and $R_5$ have the meanings as shown in Tables 1 to 16,
Het=2-chloropyridin-5-yl, $R_1$=Et and $R_2$=Me.

Tables 49 to 64

Each one of Tables 49 to 64 contains the compounds of the general formula (I-1), in which
A, $Q_1$, $Q_2$ and $R_5$ have the meanings as shown in Tables 1 to 16,
Het=2-chloropyridin-5-yl, $R_1$=Et and $R_2$=Et.

Tables 65 to 80

Each one of Tables 65 to 80 contains the compounds of the general formula (I-1), in which
A, $Q_1$, $Q_2$ and $R_5$ have the meanings as shown in Tables 1 to 16,
Het=2-chlorothiazol-5-yl, $R_1$=Me and $R_2$=Me.

Tables 81 to 96

Each one of Tables 81 to 96 contains the compounds of the general formula (I-1), in which
A, $Q_1$, $Q_2$ and $R_5$ have the meanings as shown in Tables 1 to 16,
Het=2-chlorothiazol-5-yl, $R_1$=Me and $R_2$=Et.

Tables 97 to 112

Each one of Tables 97 to 112 contains the compounds of the general formula (I-1), in which
A, $Q_1$, $Q_2$ and $R_5$ have the meanings as shown in Tables 1 to 16,
Het=2-chlorothiazol-5-yl, $R_1$=Et and $R_2$=Me.

Tables 113 to 128

Each one of Tables 113 to 128 contains the compounds of the general formula (I-1), in which
A, $Q_1$, $Q_2$ and $R_5$ have the meanings as shown in Tables 1 to 16,
Het=2-chlorothiazol-5-yl, $R_1$=Et and $R_2$=Et.

The general and the preferred definitions of radicals which have been given for the compound of the general formula (I) also apply analogously to the compounds of the remaining general formulae (intermediates or precursors).

Other preferred compounds according to the invention are addition products of acids and the substituted 1,2,3,4-tetrahydro-5-nitro-pyrimidines of the formula (I).

The acids which can be subjected to an addition reaction preferably include hydrohalic acids, such as, for example, hydrochloric acid and hydrobromic acid, in particular hydrochloric acid, furthermore phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzene-sulphonic acid, trichloroacetic acid, phthalic acid, naphthalenesulphonic acid, nicotinic acid, citric acid and ascorbic acid.

If, for example, 3-(2-chloropyridin-5-yl-methyl)-2-nitro-methylene-imidazolidine, 4-t-butylcarbamoyloxy-cyclohexylamine and at least twice the molar amount of formaldehyde are used as starting substances for process a) according to the invention, the corresponding reaction can be represented by the following equation:

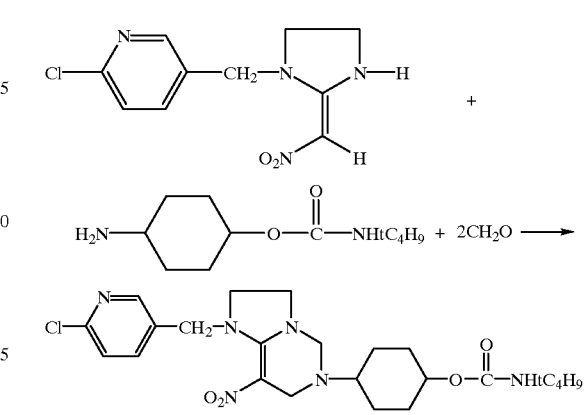

The compounds of the formula (II) to be used as starting substances in the process according to the invention are known and/or can be prepared by known methods (cf. for example German Offenlegungsschrift 2,514,402, European Offenlegungsschrift 136,636, European Offenlegungsschrift 154,178 and European Offenlegungsschrift 163,855).

The amines of the formula (III) furthermore to be used as starting substances in the process according to the invention are generally known compounds of organic chemistry.

The process according to the invention for the preparation of the new compounds of the formula (I) is preferably carried out using diluents. Diluents which are suitable are pyrimidine and thiopropyl chloroformate are used as starting substances for process b) according to the invention, the process can be represented by the following equation:

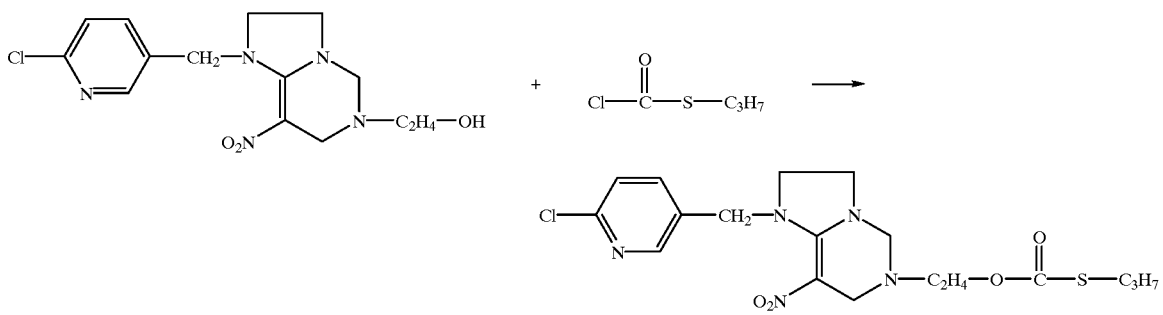

water and organic solvents which are inert in the reaction. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, and alcohols, such as methanol, ethanol, n-propanol and isopropanol. Mixtures of alcohols and water are preferably employed.

If appropriate, the process according to the invention is carried out in the presence of acidic catalysts which do not oxidise. Hydrohalic acids, such as hydrochloric acid and hydrobromic acid, phosphoric acid, and lower carboxylic acids such as acetic acid and propionic acid, have proved to be particularly useful.

When carrying out the process according to the invention, the reaction temperatures can be varied within a substantial range. In general, the process is carried out at temperatures between −20° C. and +120° C., preferably at temperatures between 0° and +80° C.

In general, the process according to the invention is carried out under atmospheric pressure. However, it can also be carried out under elevated or reduced pressure.

To carry out the process according to the invention, 1 to 1.5 mol, preferably 1 to 1.2 mol, of amine of the formula (III) and 2 to 4 mol, preferably 2 to 3 mol, of formaldehyde are employed per mole of nitromethylene derivative of the formula (II).

If appropriate, the amines of the formula (III) can be employed in the form of their aqueous solutions. Formaldehyde is employed in aqueous solution for the process according to the invention. In general, the reactions are carried out in a suitable diluent, and the reaction mixture is stirred for several hours at the temperature required in each case. Working-up in the process according to the invention is carried out in each case by customary methods.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent.

If, for example, 6,7-dihydro-6-(2-hydroxyethyl)-8-nitro-(5H)-3-(2-chloropyridin-5-yl-methyl)-imidazolidino-(2,3f)-

The compounds of the formula (IV) are known per se or can be prepared analogously to known methods (cf. European Offenlegungsschrift 375,613, 316,843, 407,594). The compounds of the formula (V) are-known.

The compounds of the formulae (IV) and (V) are preferably reacted using diluents and in the presence of a basic reaction auxiliary.

Suitable diluents for carrying out the process 2b) according to the invention are all inert organic solvents.

The following may be mentioned by way of example: halohydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; ethers, such as ethyl propyl ether, methyl tert-butyl ether, n-butyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane, dichlorodiethyl ether, nitrohydrocarbons, such as nitromethane, nitroethane, nitrobenzene, chloronitrobenzene, o-nitrotoluene; nitriles, such as acetonitrile, butyronitrile, isobutyronitrile, benzonitrile, m-chlorobenzonitrile; aliphatic, cycloaliphetic or aromatic hydrocarbons, such as heptane, hexane, nonane and cymene; benzine fractions within the boiling range of 70° C. to 190° C., cyclohexane, methylcyclohexane, petroleum ether, ligroin, octane, benzene, toluene, xylene; esters, such as ethyl acetate, isobutyl acetate; N,N-dimethylformamide, N-methyl-pyrrolidone and ketones, such as acetone or methyl ethyl ketone. Mixtures of the above-mentioned solvents and diluents are also suitable.

Ethers, such as tetrahydrofuran and dioxane, are preferred.

Basic reaction auxiliaries which can be employed are all suitable acid-binding agents, such as amines, in particular tertiary amines, as well as alkali metal compounds and alkaline earth metal compounds.

The following may be mentioned by way of example: the hydroxides, oxides and carbonates of lithium, sodium, potassium, magnesium, calcium and barium, furthermore other basic compounds such as trimethylamine, tribenzylamine, triisopropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methyl-pyrrolidone, N-methyl-piperidine, N-methyl-imidazole, N-methyl-pyrrol, N-methyl-morpholine, N-methylhexamethyleneimine, pyridine, quinoline, α-picoline, β-picoline, isoquinoline, pyrimidine, acridine, N,N,N',N'-tetra-methylenediamine, N,N,N',N'-tetraethylenediamine, quinoxaline, N-propyl-diisopropylamine, N,N'-dimethyl-cyclohexylamine, 2,6-lutidine, 2,4-lutidine, triethylenediamine, diazabicyclo-octane (DABCO), diazabi-cyclononene (DBN) or diazabicyclo-undecene (DBU).

Hydroxides of sodium and potassium or tertiary amines, such as, for example, triethylamine, tribenzylamine or trihexylamine, are preferably used.

Process 2b) is carried out by combining compounds of the formula (IV) and compounds of the formula (V) in one of the abovementioned diluents in the presence of an excess of one of the abovementioned basic reaction auxiliaries, and stirring and, if appropriate, heating, the mixture.

The reaction time is approximately 0.5 to 48 hours. The reaction is carried out at temperatures between +10° C. and +200° C., preferably between +20° C. and +150° C., particularly preferably at room temperature or the boiling point of the diluent used. The process is preferably carried out under the pressure which is established under the reaction conditions when the mixture is heated to the reaction temperature required.

To carry out the process according to the invention, 1.0 to 4.0 mol, preferably 1.0 to 2.0 mol, of compounds of the general formula (V) are generally employed per mole of compound of the formula (IV).

When the reaction is complete, the reaction mixture is, if appropriate, concentrated in vacuo (by approximately 50%), the residue is treated with aqueous acid, and the compounds of the formula (I) are worked up in a manner known per se. The products obtained can be purified in the customary manner by recrystallization, distillation in vacuo or column chromatography (cf. also the preparation examples).

The compounds of the formulae (IV), (IVa) and (IVb, c, d) which are used for carrying out process 2b) can be prepared analogously to the process described under (2a).

The compounds of the formula A used as starting compounds in process (2c) can be prepared by reacting compounds of the formula C

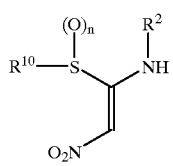

(C)

in which
$R^2$, $R^{10}$ and n can assume the abovementioned meanings as indicated in process (2a)
in the presence of at least twice the molar amount of formaldehyde, if appropriate in the presence of acidic catalysts and if appropriate in the presence of diluents, or
in the event that, in formula (1), $R^3$ represents one of the radicals

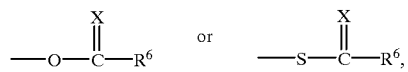

by reacting nitromethylene derivatives of the formula C with amino alcohols of the formula D

   (D)

or aminothio alcohols of the formula D'

   (D')

in which A can assume the abovementioned meaning as shown in process 2a
in the presence of at least twice the molar amount of formaldehyde, if appropriate in the presence of acidic catalysts and if appropriate in the presence of diluents, to give compounds of the formula E

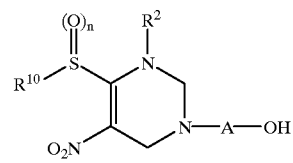

(E)

in which $R^2$, $R_{10}$, A and n have the abovementioned meanings,
and reacting these compounds with compounds of the formula (V)

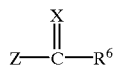

(V)

in which Z, X and $R^6$ have the abovementioned meanings or with compounds of the formula (VI)

   (VI)

in which X and $R_9$ have the abovementioned meanings,
if appropriate in the presence of an acid-binding agent and if appropriate in the presence of diluents and/or catalysts.

Amines of the formula B are known (for example EP 30 23 389; GB 22 28 003), nitromethylene derivatives of the formula C are known (FR 23 11 003; DE 26 21 092) or can be prepared analogously to known processes.

Process (2c) is carried out according to the method described in process (2b) under the conditions indicated therein.

The compounds of the formula (I) according to the invention can be employed for combating pests. Pests are undesired animal pests, in particular insects, mites and nematodes, which are harmful to plants or higher animals.

The active compounds according to the invention are suitable for combating animal pests, preferably anthropods, in particular insects, arachnids and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., Drosophila melanogaster, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The plant-parasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

For use as insecticides, acaricides and nematicides, the active compounds according to the invention can be present in their commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms inter alia.

The active compounds according to the invention can furthermore be present in their commercially available formulations and in the use forms prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary-manner appropriate for the use forms.

The compounds according to the invention are also particularly suitable for treating vegetative and generative propagation material, such as, for example, seeds of cereals, maize, vegetables and the like, or onions, nursery plants and the like.

When used against hygiene pests and pests of stored products, the active compounds are distinguished by an excellent residual action on wood and clay as well as a good stability to alkali on limed substrates.

The active substances can be applied as such, in the form of their formulations or in the form of the use forms prepared from these formulations by further dilution, such as ready-to-use solutions, suspensions, emulsions, powders, pastes and granules. They are applied in the customary manner, for example by pouring, spraying, atomizing or scattering.

The active compounds according to the invention can be applied before or after emergence of the plants.

The can also be incorporated into the soil before sowing.

The amount of active compound applied can vary within a substantial range. It depends essentially on the nature of the desired effect. In general, the application rates are between 10 g and 10 kg of active compound per hectare of soil surface, preferably between 50 g and 5 kg per ha.

To prepare the pesticides, the active compounds according to the invention can be converted into the customary formulations, such as solutions, emulsions, suspensions, powders, foams, pastes, granules, aerosols, natural and synthetic substances impregnated with active compound, very fine capsules in polymeric substances and in coating compositions for seed, and further in formulations used with burning equipment, such as fumigating cartridges, fumigating cans, fumigating coils and the like, as well as ULV cold mist and warm mist formulations.

Depending on their particular physical and/or chemical properties, the active compounds can be converted into customary formulations, such as solutions, emulsions, suspensions, powders, foams, pastes, granules, aerosols, natural and synthetic substances impregnated with active compound, very fine capsules in polymeric substances and in coating compositions for seed, and further in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxy-methylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally contain between 0.1 and 95 per cent by weight of active compound, preferably between 0.5 and 90%.

In addition to at least one compound of the general formula (I) and, if apppropriate, in addition to relevant extenders and auxiliaries, the compositions according to the invention contain at least one surface-active substance.

While having a favourable toxicity to warm-blooded species, the active compounds are also suitable for combating animal pests (ectoparasites), such as arthropods, preferably insects and arachnids (ectoparasites), which occur in animal keeping and livestock breeding, in domestic animals, productive livestock, zoo animals, laboratory animals, experimental animals and pets. In this context, they are active against all or individual stages of development of the pests and against resistant and normally-sensitive species of the pests.

By combating the animal pests, it is intended to prevent diseases and their transmission, deaths and decreasing performance (for example in the production of meat, milk, wool, hides, eggs), so that more economical and simpler animal keeping is possible or, in certain fields, only made possible, by using the active compounds.

The pests include:

From the order of the Anoplura, for example, Haematopinus spp., Linognathus spp., Solenopotes spp., Pediculus spp., Pthirus spp.;

from the order of the Mallophaga, for example, Trimenopon spp., Menopon spp., Eomenacanthus spp., Menacanthus spp., Trichodectes spp., Felicola spp., Damalinea spp., Bovicola spp.;

from the order of the Diptera, for example, Chrysops spp., Tabanus spp., Musca spp., Hydrotaea spp., Muscina spp., Haematobosca spp., Haematobia app., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera, for example, Ctenocephalides spp., Echidnophaga spp., Ceratophyllus spp.

From the order of the Metastigmata, for example, Hyalomma spp., Rhipicephalus spp., Boophilus app., Amblyomma spp., Haemophysalis spp., Dermacentor spp., Ixodes spp., Argas spp., Ornithodorus spp., Otobius spp.;

from the order of the Mesastigmata, for example, Dermanyssus spp., Ornithonyssus spp., Pneumonyssus spp.

From the order of the Prostigmata, for example, Cheyletiella spp., Psorergates spp., Myobia spp., Demodex spp., Neotrombicula spp.;

from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp., Lytodites spp., Laminosioptes spp.

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected phrophylactically as well as therapeutically.

The active compounds are administered directly or in the form of suitable preparations, enterally, parenterally, dermally, nasally, by environment treatment, or with the aid of active compound-containing shaped articles such as, for example, strips, plates, bands, collars, ear marks, limb bands, marking devices.

The active compounds are administered enterally, for example orally, in the form of powders, suppositories, tablets, capsules, pastes, drinks, granules, drenches, boli, medicated feed or drinking water. Dermal administration is effected, for example, in the form of dipping, spraying, bathing, washing, pouring-on and spotting-on and dusting. Parenteral administration is effected, for example, in the form of injection (intramuscular, subcutaneous, intravenous, intraperitoneal) or by implants.

Suitable preparations are:

Solutions such as injection solutions, oral solutions, concentrates for oral administration after dilution, solutions for use on the skin or in body cavities, pour-on and spot-on formulations, gels;

Emulsions and suspensions for oral or dermal administration and for injection; semi-solid preparations; Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injection solutions are administered intravenously, intramuscularly and subcutaneously.

Injection solutions are prepared by dissolving the active compound in a suitable solvent and, if appropriate, adding additives such as solubilizers, acids, bases, buffer salts, antioxidants and preservatives. The solutions are sterile-filtered and packaged.

The following may be mentioned as solvents: physiologically acceptable solvents such as water, alcohols such as ethanol, butanol, benzyl alcohol, glycerol, hydrocarbons, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents, which enhance dissolution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, rubbed in, splashed on or sprayed on. These solutions are prepared as described above in the case of the injectable solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and metacrylates.

Gels are applied to, or brushed onto, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systematically.

Pour-on and spot-on formulations are prepared by dissolving, suspending or emulsifying the active compound in suitable solvents or solvent mixtures which are tolerated by the skin. If appropriate, other adjuvants such as colourants, absorption accelerators, antioxidants, light stabilizers and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colourants are all colourants which are permitted for use on animals and which can be dissolved or suspended.

Examples of absorption accelerators are DMSO, spreading oils such as isopropyl myristate, dipropylene glycol perlargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

An example of a light stabilizer is novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colourants, absorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixtures with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_{8-10}$-fatty acids.

Fatty acid esters such as ethyl stearate, di-n-butyl adipate, hexyl laurate, dipropylene glycol perlargonate, esters of a branched fatty acid of medium chain length with saturated fatty alcohols of chain length $C_{16-18}$, isopropyl myristate, isopropyl palmitate, caprylic/capric esters of saturated fatty alcohols of chain length $C_{12-18}$, isopropyl stearate, oleyl oleate, decyl oleate, ethyl oleate, ethyl lactate, waxy fatty acid esters, dibutyl phthalate, diisopropyl adipate, ester mixtures related to the latter etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers; ampholytic surfactants such as disodium N-lauryl-β-imino-dipropionate or lecithin; anionic surfactants such as sodium lauryl sulphate, fatty alcohol ether sulphates, the monoethanol amine salt of mono/dialkylpolyglycol ether orthophosphoric esters; cationic surfactants such as cetyltrimethylammonium chloride.

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of an injection. They are prepared by suspending the active substance in an excipient liquid, if appropriate with the addition of further adjuvants such as wetting agents, colourants, absorption accelerators, preservatives, antioxidants and light stabilizers.

Excipient liquids which may be mentioned are all homogenous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, carcass meals, cereal meals and coarse cereal meals, and starches.

Adjuvants are preservatives, antioxidants and colourants which have already been indicated further above.

Other suitable adjuvants are lubricants and glidants such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

The present invention therefore also relates to the compounds of the general formula (I) for use as ectoparasiticides, and to the use of the compounds of the general formula (I) for the preparation of a composition for combating ectoparasites.

In the preparations, the active compounds can also be present in the form of a mixture with synergists or with other active compounds which act against pathogenic endoparasites. Examples of such active compounds are L-2,3,5,6-tetrahydro-6-phenyl-imidazothiazole, benzimidazole carbamate, praziquantel, pyrantel, febantel.

Ready-to-use preparations contain the active compound in concentrations from 10 ppm to 20 percent by weight, preferably 0.1 to 10 percent by weight.

Preparations which are diluted prior to administration contain the active compound in concentrations of 0.5–90 percent by weight, preferably 5 to 50 percent by weight.

In general, it has proved advantageous to administer amounts of approximately 1 to approximately 100 mg of active compound per kg of body weight per day, to achieve effective results.

The compounds according to the invention are preferably employed as Arthropodicides in the fields of plant protection, on domestic premises, in the hygiene field and in the protection of stored products, very particularly preferably in plant protection.

Unless otherwise specified, all percentages are by weight.

The preparation of the compounds of the general formula (I) according to the invention will be illustrated by the preparation examples which follow, and the biological activity by the biological examples which follow.

PREPARATION EXAMPLES

Example 1

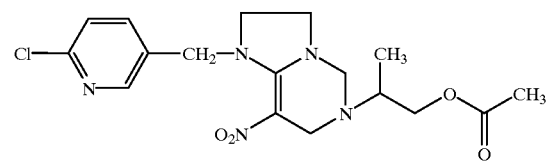

1.8 g (5 mmol) of 6,7-dihydro-6-(1-methyl-2-hydroxyethyl)-8-nitro-(5H)-3-(2-chloropyridin-5-yl-methyl)-imidazolidino-[2,3-f]-pyrimidine and 0.5 g of 4-pyrrolidino-pyridine are dissolved in 50 ml of pyridine, and 1 ml (11 mmol) of acetic anhydride is slowly added. The mixture is stirred for 4 hours at 60° C., cooled to 20° C. and poured onto approximately 50 g of ice, the mixture is extracted using dichloromethane, and the solvent is distilled off under a water pump vacuum. The residue is subsequently chromatographed on silica gel (eluent: toluene: EtOH=1:1). 1.3 g (66% of theory) of 6,7-dihydro-6-(1-methyl-2-acetyloxy-ethyl)-8-nitro-(5H)-3-(2-chloropyridin-5-yl-methyl)imidazolidino-[2,3-f]-pyrimidine are obtained.

Example 2

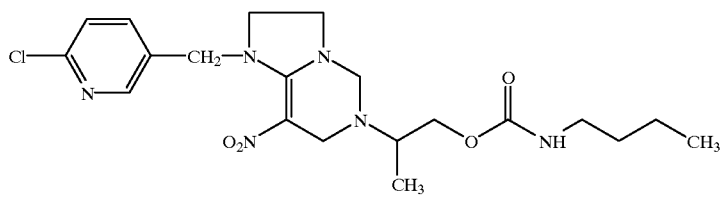

1.8 g (5 mol) of 6,7-dihydro-6-(1-methyl-2-hydroxyethyl)-8-nitro-(5H)-3-(2-chloropyridin-5-yl-methyl)-imidazolidino-[2,3-f]-pyrimidine are dissolved in 20 ml of toluene, and 1.5 ml (13 mmol) of n-butyl isocyanate and 40 mg of 1,8-diazabicyclo[5,4,0]-undec-7-ene (1,5,5) (DBU) are added at 20° C. The mixture is heated for 24 hours at 50° C., cooled and chromatographed on silica gel (eluent: toluene: acetone=1.1). 1.5 g (67% of theory) of 6,7-dihydro-6-(1-methyl-2-butylaminocarbonyl-oxy-ethyl)-8-nitro-(5H)-3-(2-chloropyridin-5-yl-methyl)-imidazolidino-[2,3-f]-pyrimidine are obtained.

Example 3

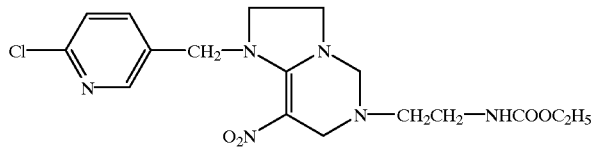

4.5 ml of a 30% strength formaldehyde solution are added dropwise at 20° C. to a mixture of 6.4 g (0.025 mol) of 3-(2-chloro-pyridin-5-yl-methyl)-2-nitromethylene-imidazolidine and 3.6 g (0.027 mol) of 1-amino-2-ethoxycarbonyl-amino-ethane in 25 ml of ethanol. The mixture is stirred for 2 hours under reflux and cooled to 20° C., and most of the solvent is distilled off under a water pump vacuum. The product is subsequently chromatographed on silica gel. 8 g (82% of theory) of 6,7-dihydro-6-(2-ethoxy-carbonylamino-ethyl)-8-nitro-(5H)-3-(2-chloropyridin-5-yl-methyl)-imidazolidino-[2,3-f] -pyrimidine having a melting range of 46 to 48° C. are obtained.

The following compounds of the formula (I) are prepared analogously.

| Ex. No. | Het | $R^1$ | $R^2$ | A—$R^3$ | Physical Data |
|---|---|---|---|---|---|
| 4 | Cl-pyridyl | $C_2H_5$ | $CH_3$ | —$(CH_2)_3OCONHC_4H_9$-n | see appendix |
| 5 | Cl-pyridyl | $C_2H_5$ | $CH_3$ | —$(CH_2)_2NHCOCH_3$ | see appendix |
| 6 | Cl-pyridyl | $C_2H_5$ | $CH_3$ | —$(CH_2)_3OCOCH_3$ | see appendix |
| 7 | Cl-pyridyl | —$CH_2CH_2$— | | —$(CH_2)_3OCONHC_3H_7$-i | see appendix |
| 8 | Cl-pyridyl | —$CH_2CH_2$— | | —$(CH_2)_3OCONH(CH_2)_6Cl$ | see appendix |

-continued

| Ex. No. | Het | R¹ R² | A—R³ | Physical Data |
|---|---|---|---|---|
| 9 | 2-Cl-5-pyridyl | —CH₂CH₂— | —(CH₂)₃OCONHC₄H₉-t | see appendix |
| 10 | 2-Cl-5-pyridyl | —CH₂CH₂— | —(CH₂)₃OCONHCH₂C₄H₉-t | see appendix |
| 11 | 2-Cl-5-pyridyl | —CH₂CH₂— | —(CH₂)₃OCONHC₄H₉-n | see appendix |
| 12 | 2-Cl-5-pyridyl | —CH₂CH₂— | —(CH₂)₃OCONHC₄H₉-i | see appendix |
| 13 | 2-Cl-5-pyridyl | —CH₂CH₂— | —(CH₂)₂OCONH(CH₂)₆Cl | see appendix |
| 14 | 2-Cl-5-pyridyl | —CH₂CH₂— | —(CH₂)₂OCONHC₃H₇-i | See appendix |
| 15 | 2-Cl-5-pyridyl | —CH₂CH₂— | —(CH₂)₃OCOC₂H₅ | |
| 16 | 2-Cl-5-pyridyl | —CH₂CH₂— | —(CH₂)₂NHCOOC₄H₉-t | mp. 127–129° C. |
| 17 | 2-Cl-5-pyridyl | —CH₂CH₂— | —(CH₂)₂NHCOCH₃ | mp. 68–70° C. |
| 18 | 2-Cl-5-pyridyl | —CH₂CH₂— | —(CH₂)₂NHCOOCH₂C₆H₅ | mp. 68–70° C. |
| 19 | 2-Cl-5-pyridyl | —CH₂CH₂— | —(CH₂)₂—NHCOOC₂H₅ | |
| 20 | 2-Cl-5-pyridyl | —CH₂CH₂— | —(CH₂)₂OCONHCH₃ | mp. 154–156° C. |
| 21 | 2-Cl-5-pyridyl | —CH₂CH₂— | —(CH₂)₂CO-(2-imidazolyl) | |

-continued

| Ex. No. | Het | R¹ R² | A—R³ | Physical Data |
|---|---|---|---|---|
| 22 | 2-Cl-5-pyridyl | —CH₂CH₂— | —(CH₂)₂OCONHCH₃ | |
| 23 | 2-Cl-5-pyridyl | —CH₂CH₂— | —(CH₂)₃OCOCH₃ | mp. 118–120° C. |
| 24 | 2-Cl-5-pyridyl | —CH₂CH₂— | —(CH₂)₂OCOCH₃ | |
| 25 | 2-Cl-5-pyridyl | —CH₂CH₂— | —CH(CH₃)CH₂OCONHC₄H₉-n | |
| 26 | 2-Cl-5-pyridyl | —CH₂CH₂ | —(CH₂)₄NHCOOCH₂C₆H₅ | |
| 27 | 2-Cl-5-pyridyl | —CH₂CH₂ | —(CH₂)₂OCONHC₄H₉n | see appendix |
| 28 | 2-Cl-5-pyridyl | —CH₂CH₂ | —CH₂—CH(C₆H₅)—O—C(=O)—NHC₄H₉n | mp. 78–82° C. |
| 29 | 2-Cl-5-pyridyl | —CH₂CH₂ | —CH₂—CH(CH₃)—O—C(=O)—C₄H₉-n | |
| 30 | 2-Cl-5-pyridyl | —CH₂CH₂ | —CH₂—CH(CH₃)—O—C(=O)—CH₃ | |
| 31 | 2-Cl-5-pyridyl | —CH₂CH₂ | —(CH₂)₃—O—C(=O)—NH(CH₂)₂—O—CH₃ | lg P = 1.11 (acidic) |
| 32 | 2-Cl-5-pyridyl | —CH₂CH₂ | —(CH₂)₂—O—C(=O)—NH(CH₂)₂—O—(CH₂)₂—OC₂H₅ | lg P = 1.26 (acidic) |
| 33 | 2-Cl-5-pyridyl | —CH₂CH₂ | —(CH₂)₂—O—C(=O)—NH—CH(CH₃)—CH₂—O—C₄H₉t | lg P = 2.26 (neutral) |

Furthermore compounds of the following formula

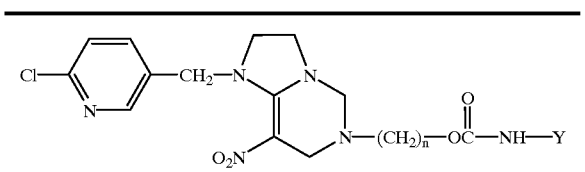

| Ex. No. | N | Y | Physical Data |
|---|---|---|---|
| 34 | 5 | —(CH$_2$)$_2$—O—(CH$_2$)$_2$—OCH$_3$ | lg P = 1.28 |
| 35 | 5 | —(CH$_2$)$_2$—O—(CH$_2$)$_2$—OC$_2$H$_5$ | lg P = 1.44 |
| 36 | 5 | —(CH$_2$)$_2$—OCH$_3$ | lg P = 1.24 |
| 37 | 5 | —C$_6$H$_4$—SO$_2$—CF$_3$ | lg P = 2.29 |
| 38 | 5 | —C$_6$H$_5$ | lg P = 1.79 |
| 39 | 5 | —(CH$_2$)$_2$—OCOCH$_3$ | lg P = 0.82 |
| 40 | 5 | —(CH$_2$)$_2$—OCOC$_4$H$_9$-t | lg P = 1.81 |
| 41 | 5 | —C$_6$H$_4$—Cl | lg P = 2.09 |
| 42 | 5 | —C$_6$H$_3$Cl$_2$ | mp: 58–60° C. |
| 43 | 5 | —CH$_2$—C$_4$H$_9$-t | lg P = 2.01 |
| 44 | 5 | —C$_6$H$_4$—SCF$_3$ | lg P = 2.74 |
| 45 | 5 | —CH$_2$—C(CH$_3$)$_2$—OCH$_3$ | lg P = 1.56 |
| 46 | 6 | —(CH$_2$)$_2$—O—(CH$_2$)$_2$—OCH$_3$ | lg P = 1.47 |
| 47 | 6 | —(CH$_2$)$_2$—O—(CH$_2$)$_2$—OC$_2$H$_5$ | lg P = 1.63 |
| 48 | 6 | —(CH$_2$)$_2$—OCH$_3$ | lg P = 1.44 |
| 49 | 6 | —C$_6$H$_4$—SO$_2$—CF$_3$ | lg P = 2.51 |
| 50 | 6 | —C$_6$H$_5$ | lg P = 2.01 |
| 51 | 6 | —(CH$_2$)$_2$—OCOCH$_3$ | lg P = 1.47 |
| 52 | 6 | —(CH$_2$)$_2$—OCOC$_4$H$_9$-t | lg P = 1.98 |
| 53 | 6 | —C$_6$H$_4$—Cl | lg P = 2.27 |

-continued

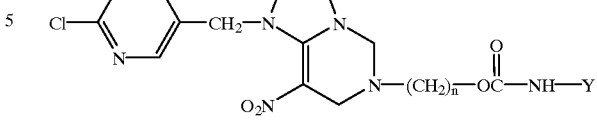

| Ex. No. | N | Y | Physical Data |
|---|---|---|---|
| 54 | 6 | —C$_6$H$_3$Cl$_2$ | lg P = 2.59 |
| 55 | 6 | —CH$_2$—C$_4$H$_9$-t | lg P = 2.05 |
| 56 | 6 | —C$_6$H$_4$—SCF$_3$ | lg P = 2.71 |
| 57 | 6 | —CH$_2$—C(CH$_3$)$_2$—OCH$_3$ | lg P = 1.60 |
| 58 | 4 | —(CH$_2$)$_2$—O—(CH$_2$)$_2$—OCH$_3$ | lg P = 1.20 |
| 59 | 4 | —(CH$_2$)$_2$—O—(CH$_2$)$_2$—OC$_2$H$_5$ | lg P = 1.36 |
|    |   | —(CH$_2$)$_2$—OCH$_3$ | lg P = 1.24 |
| 60 | 4 | —C$_6$H$_4$—SO$_2$—CF$_3$ | lg P = 2.22 |
| 61 | 4 | —C$_6$H$_5$ | lg P = 1.72 |
| 62 | 4 | —(CH$_2$)$_2$—OCOCH$_3$ | lg P = 1.22 |
| 63 | 4 | —(CH$_2$)$_2$—OCOC$_4$H$_9$-t | lg P = 1.73 |
| 64 | 4 | —C$_6$H$_4$—Cl | lg P = |
| 65 | 4 | —C$_6$H$_3$Cl$_2$ | lg P = 1.53 |
| 66 | 4 | —CH$_2$—C$_4$H$_9$-t | lg P = 1.75 |
| 67 | 4 | —C$_6$H$_4$—SCF$_3$ | lg P = |
| 68 | 4 | —CH$_2$—C(CH$_3$)$_2$—OCH$_3$ | lg P = |
| 69 | 5 | CH$_3$ | lg P = |
| 70 | 6 | CH$_3$ | lg P = |
| 71 | 4 | CH$_3$ | lg P = |
| 72 | 3 | CH$_3$ | Mp: 154–156° C. |
| 73 | 4 | C$_4$H$_9$-n | Mp: 106° C. |

Furthermore compounds of the formula I, in which the radicals have the following meaning:

| Ex. No. | Het | R¹ | R² | A—R³ | Physical Data |
|---|---|---|---|---|---|
| 74 | 2-Cl-pyridin-5-yl | —CH₂—CH₂— | | phenyl-CH(CH₂CH₃)—O—C(=O)—NHC₄H₉-n | Mp: 78–82° C. |
| 75 | 2-Cl-pyridin-5-yl | —CH₂—CH₂— | | CH₃-CH(CH₂CH₃)—O—C(=O)—NHC₄H₉-n | lg P = 1.63 |
| 76 | 2-Cl-pyridin-5-yl | —CH₂—CH₂— | | —(CH₂)₄—O—C(=O)—CH₃ | Mp: 138° C. |
| 77 | 2-Cl-thiazol-5-yl | —CH₂—CH₂— | | —(CH₂)₆—OC(=O)NHC₄H₉n | Fp: 114 |
| 78 | 2-Cl-thiazol-5-yl | —CH₂—CH₂— | | —(CH₂)₅—OC(=O)NHC₄H₉n | Fp: >200° C.<br>log P: 1.73 |
| 79 | 2-Cl-thiazol-5-yl | —CH₂—CH₂— | | —(CH₂)₆—OC(=O)NHC₄H₉t | log P: 1.90 |

Appendix to Table 1:

Example No. 12 ¹H NMR (DMSO) δ=0.8 (6H;d), 1.4–1.8 (3H, m), 2.50 (2H, m), 2.82 (2H, m), 3.60 (6H, m), 3.95 (2H, t), 4.05 (2H, s), 4.80 (2H, s), 6.4 (1H, br), 7.50 (1H, d), 7.80 (1H, dd), 8.40 (1H, d).

Example No. 9 ¹H NMR (DMSO) δ=1.20 (9H,s), 1.70 (2H, m), 2.50 (2H, m), 3.65 (6H, m), 3.95 (2H, t), 4.08 (2H, s), 4.80 (2H, s), 6.70 (1H, br), 7.50 (1H, d), 7.85 (1H, dd), 8.38 (1H, d).

Example No. 4 NMR (DMSO) δ=8.34 (d, 1H), 7.77 (dd, 1H), 7.49 (d, 1H), 7.07 (t, 1H), 4.38 (AB, 2H), 3.78 (9, 2H), 0.86 (t, 3H).

Example No. 5 ¹H NMR (CDCl₃) δ=8.3 (d, 1H), 7.68 (dd, 1H), 7.33 (d, 1H), 6.07 (br t, 1H), 4.35 (AB, 2H), 3.02 (s, 3H), 2.02 (s, 3H), 1.21 (t, 3H).

Example No. 6 ¹H NMR (DMSO) δ=8.33 (d, 1H), 7.77 (dd, 1H), 7.49 (d, 1H), 4.37 (AB, 2H), 3.13 (m, 1H), 1.99 (s, 3H), 1.74 (m, 2H), 1.18 (t, 3H).

Example No. 7 ¹H NMR (DMSO) δ=1.05 (6H, d) 2.70 (2H, m), 2.50 (2H, m), 3.5–3.7 (9H, m), 3.95 (2H, t), 4.05 (2H, s), 4.80 (2H, s), 6.85 (1H, br), 7.50 (1H, d), 7.85 (1H, dd), 8.40 (1H, d).

Example No. 8 ¹H NMR (DMSO) δ=1.2–1.4 (6H, m,), 1.6–1.8 (4H, m), 2.5 (2H, m), 2.95 (2H, m), 3.5–3.7 (6H, m), 3.95 (2H, t), 4.05 (2H, s), 4.80 (2H, s), 7.0 (1H, br), 7.5 (1H, d), 7.85 (1H, dd), 8.38 (1H, d).

Example No. 10 ¹H NMR (DMSO) δ=0.8 (9H, s), 1.70 (2H, m), 2.50 (2H, m), 2.80 (2H, s), 3.20 (2H, m), 3.65 (4H, m), 3.95 (2H, t), 4.05 (2H, s), 4.80 (2H, s), 7.0 (1H, br), 7.5 (1H, d), 7.85 (1H, dd), 8.40 (1H, d).

Example No. 11 ¹H NMR (DMSO) δ=0.85 (3H, t), 1.1–1.5 (4H, m), 1.70 (2H, m), 2.5 (2H, m), 2.95 (2H, m), 3.65 (6H, m), 3.95 (2H, t), 4.05 (2H, s), 4.80 (2H, s), 6.95 (1H, br), 7.50 (1H, d), 7.85 (1H, dd), 8.38 (1H, d).

Example No. 13 ¹H NMR (DMSO) δ=1.2–1.4 (6H, m), 1.6–1.8 (2H, m), 2.70 (2H, m), 2.95 (2H, m), 3.6–3.7 (8H, m), 4.0–4.2 (4H, m), 4.8 (2H, s), 7.0 (H, br), 7.50 (1H, d), 7.85 (1H, dd), 8.4 (1H, d).

Example No. 14 ¹H NMR (DMSO) δ=1.0 (6H, d), 2.65 (2H, m), 3.5–3.8 (7H, m), 4.0–4.2 (4H, m), 4.8 (2H, s), 6.95 (1H, br), 7.5 (1H, d), 7.85 (1H, dd), 8.40 (1H, d).

Example No. 27 ¹H NMR (DMSO) δ=0.85 (3H, t), 1.2–1.5 (4H, m), 2.70 (2H, m), 2.95 (2H, m), 3.6–3.7 (4H, m), 4.0–4.2 (4H, m), 4.3 (2H, s), 4.8 (2H, s), 7.0 (1H, br), 7.5 (1H, d), 7.85 (1H, dd), 8.40 (1H, d).

Preparation of the starting compounds of the formula (IV)

Example II-1

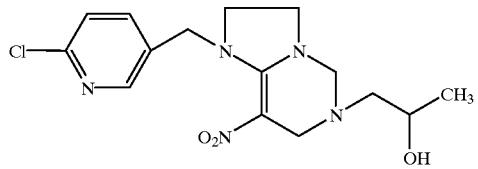

4.5 ml of a 30% strength formaldehyde solution are added dropwise at 20° C. to a mixture of 6.4 g (0.025 mol) of 3-(2-chloropyridin-5-yl-methyl)-2-nitromethylene-imidazolidine and 2.0 g (0.027 mol) of 1-amino-2-propanol in 25 ml of ethanol. The mixture is refluxed for four hours and then cooled to room temperature, ethanol is distilled off under a water pump vacuum, and the residue is chromatographed (eluent: methylene chloride: ethanol=1:1). 5.5 g (63% of theory) of 6,7-dihydro-6-(2-hydroxypropyl)-8-nitro-(5H)-3-(2-chloropyridin-5-yl-methyl)-imidazolidino-[2,3-f]-pyrimidine having a melting range of 156–158° C. are obtained.

Example II-2

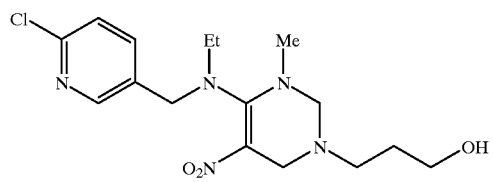

9.6 g (37 mmol) of 1-[N-(6-chloro-3-pyridyl)-N-ethyl] amino-1-methylamino-2-nitroethylene (EP 302,389) were suspended in 100 ml of ethanol. After addition of 3.33 g (44 mmol) of 3-amino-1-propanol and 7.6 ml (101 mmol) of 37% strength aqueous formaldehyde solution, the mixture was refluxed for 4 hours. Chromatography of the residue obtained after the solvent had been distilled off gave 8.9 g (63%) of the title compound as a yellow oil.

NMR (d-DMSO]: 8.33 (d, 1H), 7.77 (dd, 1H), 7.49 (d, 1H), 4.49–4.24 (m, 3H), 4.11 (q, 2H), 3.37 ('q', 2H), 1.56 (quint, 2H), 1.12 (t, 3H).

The intermediates of the formula (II) of Table 2 below are obtained analogously:

TABLE 2

| Ex. No. | A | R | Physical Data |
|---|---|---|---|
| II-3 | 6-chloro-3-pyridyl | —CH(CH$_3$)—CH$_2$—OH | $^1$H NMR(DMSO): δ=0.95 ppm, 2.7 ppm, 3.3 ppm, 3.5–3.8 ppm, 4.1–4.8 ppm, 7.6–8.4 ppm |
| II-4 | 6-chloro-3-pyridyl | —CH$_2$—CH$_2$—OH | |
| II-5 | 6-chloro-3-pyridyl | —CH(Ph)—CH$_2$—OH | 74–76° C. 80° C. |
| II-6 | 6-chloro-3-pyridyl | —CH$_2$—CH(CH$_3$)—OH | 156–158° C. |
| II-7 | 2-chloro-5-thiazolyl | —CH$_2$—CH(CH$_3$)—OH | 128–130° C. |
| II-8 | 2-chloro-5-thiazolyl | —CH(CH$_3$)—CH$_2$—OH | 64–66° C. |
| II-9 | 2-chloro-5-thiazolyl | —CH$_2$—CH(Ph)—OH | 65° C. |

TABLE 2-continued

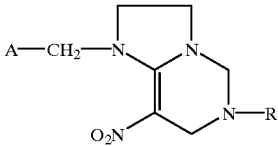

| Bsp. Nr. | A | R | phys. Daten |
|---|---|---|---|
| II-10 | 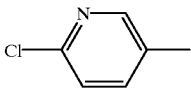 | —CH₂CH₂CH₂—OH | |
| II-11 | 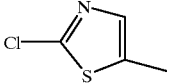 | —CH₂CH₂CH₂—OH | ¹H NMR(DMSO): δ: 1.8 ppm, 2.7 ppm, 3.6–4.1 ppm, 4.9 ppm, 7.5 ppm |
| II-12 | 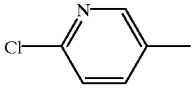 | —CH₂CH₂CH₂CH₂—OH | 98–100° C. |
| II-13 | 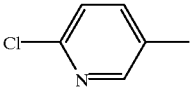 | —(CH₂)₅—OH | lg P = 0.97, acidic |
| II-14 | 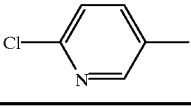 | —(CH₂)₆—OH | lg P = 0.74 |

| Bsp. Nr. | A | R | phys. Daten |
|---|---|---|---|
| II-15 | 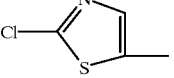 | —(CH₂)₆—OH | lg P = 0.94 |
| II-16 | 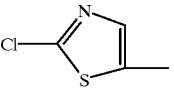 | —(CH₂)₅—OH | lg P = 0.71 |
| II-17 | 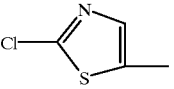 | —(CH₂)₄—OH | lg P = 0.58 |

Example A

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars have been killed.

In this test, superior activity compared with the prior art is shown, for example, by the following compounds of the preparation examples:

TABLE A
(Plant-injurious insects)
Plutella-Test
| Active compounds | Active compound concentration in % | Degree of destruction in % after 3d |
|---|---|---|
| 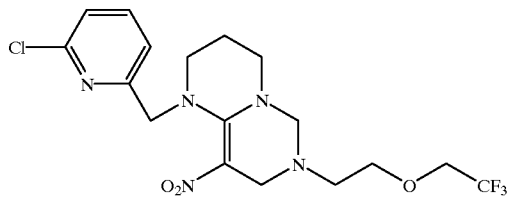 | 0.1<br>0.01 | 100<br>0 |
| 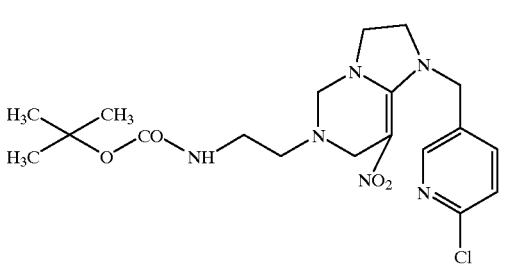 | 0.1<br>0.01 | 100<br>100 |
| 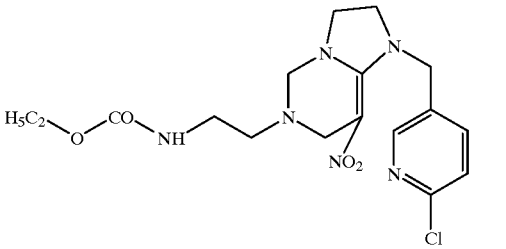 | 0.1<br>0.01 | 100<br>100 |
| 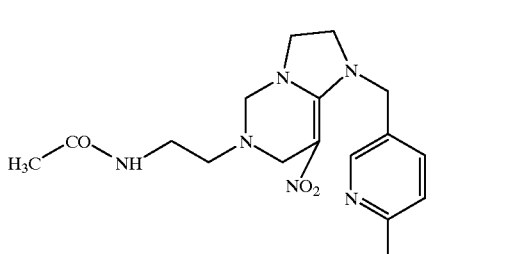 | 0.1<br>0.01 | 100<br>100 |
| 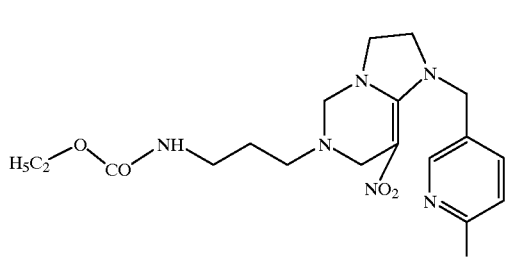 | 0.1<br>0.01 | 100<br>100 |

TABLE A-continued
(Plant-injurious insects)
Plutella-Test
| Active compounds | Active compound concentration in % | Degree of destruction in % after 3d |
|---|---|---|
| 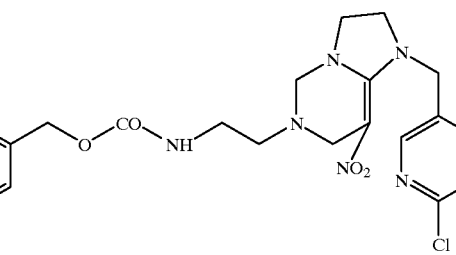 | 0.1<br>0.01 | 100<br>100 |
| 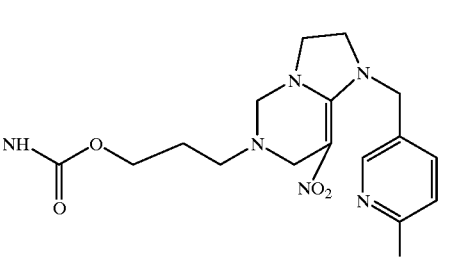 | 0.1<br>0.01 | 100<br>100 |
| 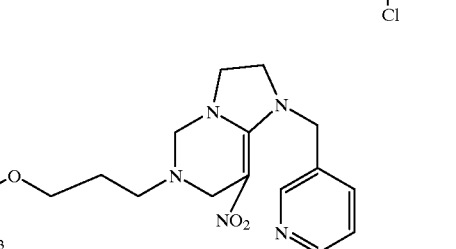 | 0.1<br>0.01 | 100<br>100 |
| 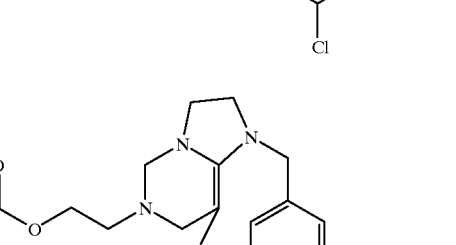 | 0.1<br>0.01 | 100<br>100 |
| 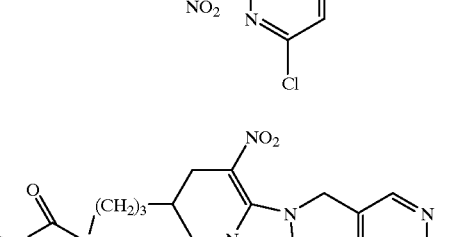 | 0.1<br>0.01 | 100<br>100 |
| 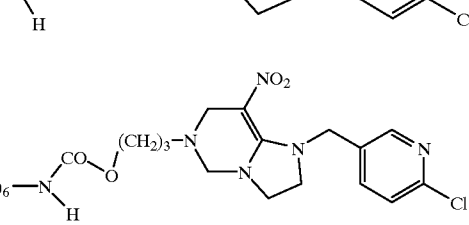 | 0.1<br>0.01 | 100<br>100 |

TABLE A-continued (Plant-injurious insects)
Plutella-Test

| Active compounds | Active compound concentration in % | Degree of destruction in % after 3d |
|---|---|---|
| 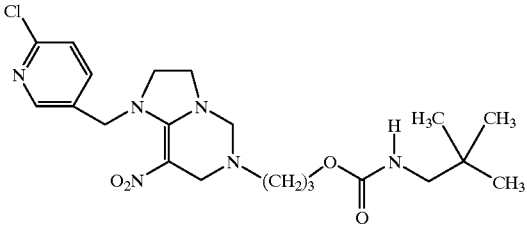 | 0.1<br>0.01 | 100<br>100 |

Example B

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leafhopper (*Nephotettix cincticeps*) while the seedlings are still moist.

After the desired period of time, the destruction in % is determined. 100% means that all the leafhoppers have been killed; 0% means that none of the leafhoppers have been killed.

In this test, superior activity compared with the prior art is shown, for example, by the following compounds of the preparation examples:

TABLE B (Plant-injurious insects)
Nephotettix-test

| Active compounds | Active compound concentration in % | Degree of destruction in % after 6d |
|---|---|---|
| 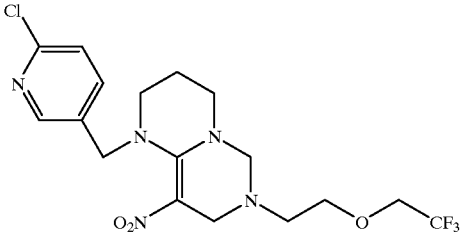<br>known | 0.001<br>0.0001<br>0.00001 | 100<br>60<br>0 |
| 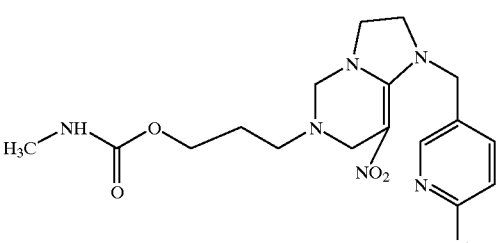 | 0.001<br>0.0001<br>0.00001 | 100<br>100<br>100 |

TABLE B-continued (Plant-injurious insects)
Nephotettix-test

| Active compounds | Active compound concentration in % | Degree of destruction in % after 6d |
|---|---|---|
| [structure: acetate-O-(CH2)3-N linked to bicyclic system with NO2, CH2-pyridine-Cl] | 0.001<br>0.0001<br>0.00001 | 100<br>100<br>100 |

Example C

Myzus test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach aphid (*Myzus persicae*) are treated by being dipped into the preparation of active compound of the desired concentration.

After the desired period of time, the destruction in % is determined. 100% means that all the aphids have been killed; 0% means that none of the aphids have been killed.

In this test, superior activity compared with the prior art is shown, for example, by the following compounds of the preparation examples:

TABLE C (Plant-injurious insects)
Myzus-Test

| Active compounds | Active compound concentration in % | Degree of destruction in % after 6d |
|---|---|---|
| [structure with Cl-pyridine-CH2-N, bicyclic with O2N, N-CH2CH2-O-CH2-CF3] known | 0.01<br>0.001 | 80<br>0 |
| [structure: (H3C)3C-O-CO-NH-CH2CH2-N linked to bicyclic system with NO2, CH2-pyridine-Cl] | 0.01<br>0.001 | 100<br>100 |

TABLE C-continued
(Plant-injurious insects)
Myzus-Test
| Active compounds | Active compound concentration in % | Degree of destruction in % after 6d |
|---|---|---|
| 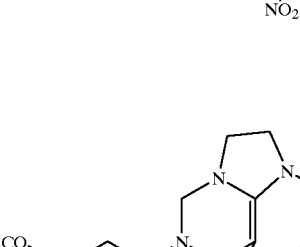 | 0.01<br>0.001 | 100<br>95 |
| 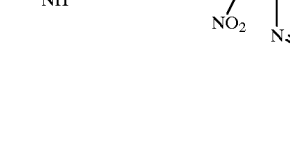 | 0.01<br>0.001 | 100<br>100 |
| 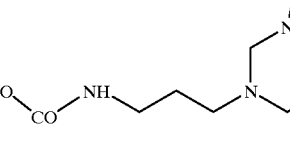 | 0.01<br>0.001 | 100<br>99 |
| 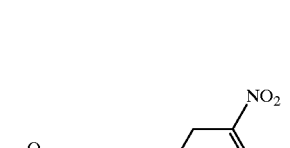 | 0.01<br>0.001 | 100<br>99 |
| 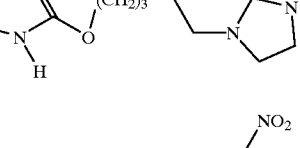 | 0.01<br>0.001 | 100<br>100 |
| 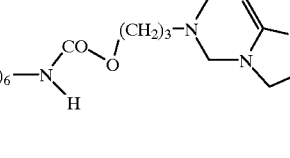 | 0.01<br>0.001 | 100<br>98 |

Example D

Critical concentration test/root-systemic action
Test insect: *Aphis fabae*
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with pregerminated broad beans. The active compound can in this way be taken up from the soil by the roots of the plants and be transported into the leaves.

To demonstrate the root-systemic effect, the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

Active compounds, application rates and results can be seen in the table which follows:

TABLE D

Root-systemic action
Aphis fabae

| Active compound (Constitution) | Degree of destruction in % at active compound concentrations in ppm |
|---|---|
| 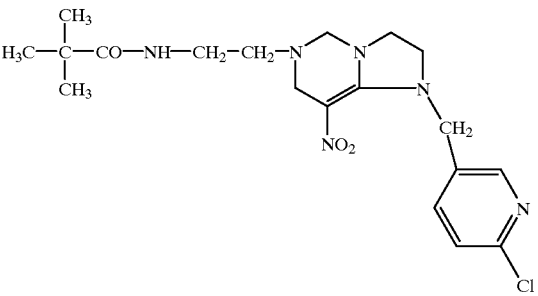 | 20 ppm = 100% |

Example E

Test with resistant *Lucilia cuprina* larvae
Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm³ of horse meat and 0.5 ml of the preparation of active compound. After 24 hours, the degree of destruction is determined.

In this test, a superior activity compared with the prior art, and an effectiveness of 100% at 100 ppm, was shown, for example, by the following compounds of the preparation examples: 3, 16, 18, 14.

Example F

In-vitro flea test (all stages of development)
Test object: All stages (eggs, larvae, pupae and adults) of *Ctenocephalides felis*.
Test method: Bloodmeal is dried overnight in a shallow dish at approximately 70° C. and subsequently screened using a mesh size of 0.63 mm.

1.8 g portions of the bloodmeal which has been prepared in this manner are placed into plastic Petri dishes ø 9.8 cm.

Using an Eppendorf pipette, 0.2 ml of the substance are added to the 1.8 g portions of bloodmeal (dilution 1:10). This means that for a use concentration of 1 ppm, the aqueous solution must have a concentration of 10 ppm. The solution is applied dropwise and uniformly over the entire area covered by the bloodmeal.

The dishes which have been prepared in this manner are allowed to dry overnight. Using a suitable device, the substance, now in the form of dried lumps of bloodmeal, is broken up and distributed homogeneously in the Petri dish by swirling. To the test dishes which have been prepared in this manner there is now added a spatula—tipful of flea eggs which have been obtained by screening (and which are derived from experimentally infected cats). The dish is sealed using Parafilm and shaken vigorously.

The test materials are incubated at 25° C. and a relative humidity of 85%. At certain intervals, the dishes are examined for stages of development of the fleas.

Test criterion: The criterion for the in-vitro activity of a substance is defined as the inhibition of flea development, or a standstill during the development before reaching the adult stage.

Assessment:
  Effective: No adult fleas found after 1½ times the development time.
  Ineffective: Adult fleas found after 1½ times the development time.

An activity of 100% is shown, in this test, by the compounds of Examples 3, 16, 18 and 19 at 10 ppm.

Fly test G
Test animals: Musca domestics, strain WHO(N)
Solvent: 35 parts by weight of ethylene glycol mono-methyl ether
  35 parts by weight of nonylphenol polyglycol ether To produce a suitable formulation, three parts by weight of active compound are mixed with seven parts of the abovementioned solvent-emulsifier mixture and the emulsion concentrate thus obtained is diluted with water to the particular desired concentration.

2 ml of this preparation of active compound are pipetted onto paper filter discs (ø 9.5 cm) located in Petri dishes of a suitable size. After the discs have dried, 25 test animals are transferred into the Petri dishes and covered.

After 6 hours, the activity of the preparation of active compound is determined. The activity is expressed in %. 100% means that all flies have been destroyed; 0% means that no flies have been destroyed.

In this example, compound 16 shows an activity of 100% at 1000 ppm.

We claim:

1. Substituted 1,2,3,4-tetrahydro-5-nitro-pyrimidines of the formula (I)

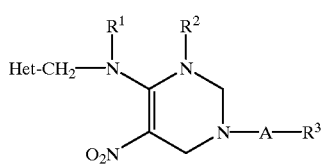

(I)

wherein

Het represents

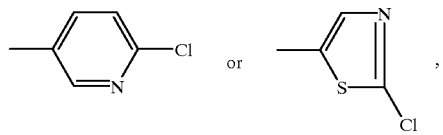

$R^1$ and $R^2$ represent ethylene;

A represents ethylene, propylene or butylene, each of which can optionally be substituted by halogen or by phenyl, and A furthermore represents cyclohexylene;

$R^3$ represents

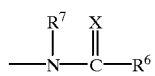

wherein $R^6$ represents a $C_1$–$C_6$ alkyl, or an amino radical;

$R^7$ represents hydrogen or a $C_1$–$C_4$ alkyl; and

X represents sulphur or oxygen.

2. A process for the preparation of substituted 1,2,3,4-tetrahydro-5-nitro-pyrimidines of the formula (I) according to claim 1, in which Het, $R^1$, $R^2$, A, $R^3$, $R^6$, $R_7$, and X are as defined in claim 1, wherein nitromethylene derivatives of the formula (II)

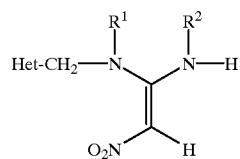

(II)

in which

Het, $R^1$ and $R^2$ are as defined above, are reacted with amines of the formula (III),

(III)

in which

A and $R^3$ are as defined above, in the presence of at least twice the molar amount of formaldehyde, if appropriate in the presence of acidic catalysts and if appropriate in the presence of diluents.

3. An insecticidal or ectoparasiticidal composition which comprises an amount of a compound according to claim 1 effective for combatting said insects or ectoparasites and an inert carrier.

4. A method of combatting insects or ectoparasites which comprises administering or applying to said insects or ectoparasites or to an environment from which it is desired to exclude said insects or ectoparasites an amount of a compound according to claim 1 effective for combatting said insects or ectoparasites.

5. Nitromethylene derivatives of the formulae (IVb), (IVc) and (IVd)

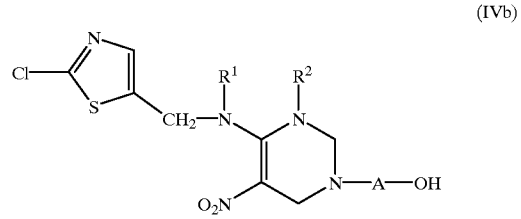

(IVb)

in which $R^1$, $R^2$ and A have the meanings given in claim 1,

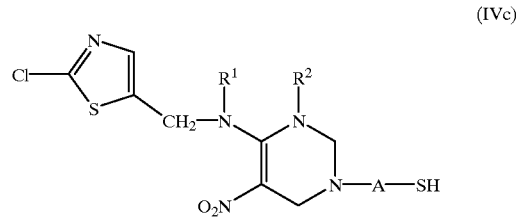

(IVc)

in which $R^1$, $R^2$ and A have the meanings given in claim 1,
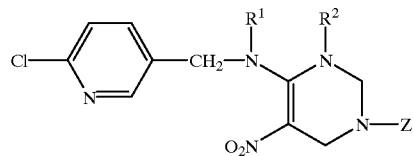
(IVd)
in which
$R^1$ and $R^2$ have the meanings given in claim 1 and Z represents
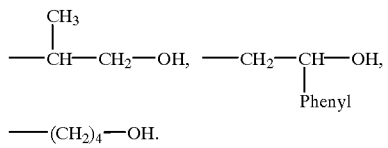
—(CH$_2$)$_4$—OH.